United States Patent
Shechter

(10) Patent No.: US 8,121,374 B2
(45) Date of Patent: Feb. 21, 2012

(54) BANDS ARTIFACT REDUCTION FOR CARDIAC CT IMAGING

(75) Inventor: Gilad Shechter, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1099 days.

(21) Appl. No.: 11/917,770

(22) PCT Filed: Jun. 13, 2006

(86) PCT No.: PCT/IB2006/051889
§ 371 (c)(1),
(2), (4) Date: Dec. 17, 2007

(87) PCT Pub. No.: WO2006/136973
PCT Pub. Date: Dec. 28, 2006

(65) Prior Publication Data
US 2008/0193003 A1  Aug. 14, 2008

Related U.S. Application Data

(60) Provisional application No. 60/692,753, filed on Jun. 22, 2005.

(51) Int. Cl.
*G06K 9/20* (2006.01)

(52) U.S. Cl. ........................................... 382/131

(58) Field of Classification Search ............... 378/4, 15, 378/19, 38, 210, 901; 382/131, 132
See application file for complete search history.

(56) References Cited

U.S. PATENT DOCUMENTS

| | | | |
|---|---|---|---|
| 6,104,775 A | 8/2000 | Tuy | |
| 6,522,712 B1 | 2/2003 | Yavuz et al. | |
| 6,597,803 B1 | 7/2003 | Pan et al. | |
| 6,819,736 B1 | 11/2004 | Bruder et al. | |

(Continued)

FOREIGN PATENT DOCUMENTS

WO 2004089217 A1 10/2004

OTHER PUBLICATIONS

Grass, et al., "Helical Cardiac Cone Beam Reconstruction Using Retrospective ECG Gating," Phys. Med. Biol. 48 (2003) 3069-3084.

(Continued)

*Primary Examiner* — Irakli Kiknadze

(57) ABSTRACT

A subject is imaged at a preselected phase point (34) which occurs in one or more successive cardiac cycles as the subject moves in an examination region (16). An illumination window (94) illuminates each reconstructed voxel (A, B, C) of the subject in phase point windows (92) adjacent surroundingly the preselected phase point (34). A temporal window (90) is determined which includes an integer number N of successive cardiac cycles, in which the phase point windows (92) are entirely included in the illumination window (94). The illumination window (94) is truncated in accordance with the determined temporal window (90). First and second regions (72, 74) are determined along an axial direction (Z), the first and second regions (72, 74) alternating with one another. A temporal weighting profile processor (64) generates a projection dependent temporal weighting profile (66). A temporal window processor (102) applies the normalized backprojection weights for each voxel which lies in an associated first region. A varying weight processor (110) continuously smoothly weights readings for each voxel lying in an associated second region (74). A backprojection processor (120) three-dimensionally backprojects the weighted readings into a volumetric image representation.

20 Claims, 3 Drawing Sheets

U.S. PATENT DOCUMENTS

Figure 1:
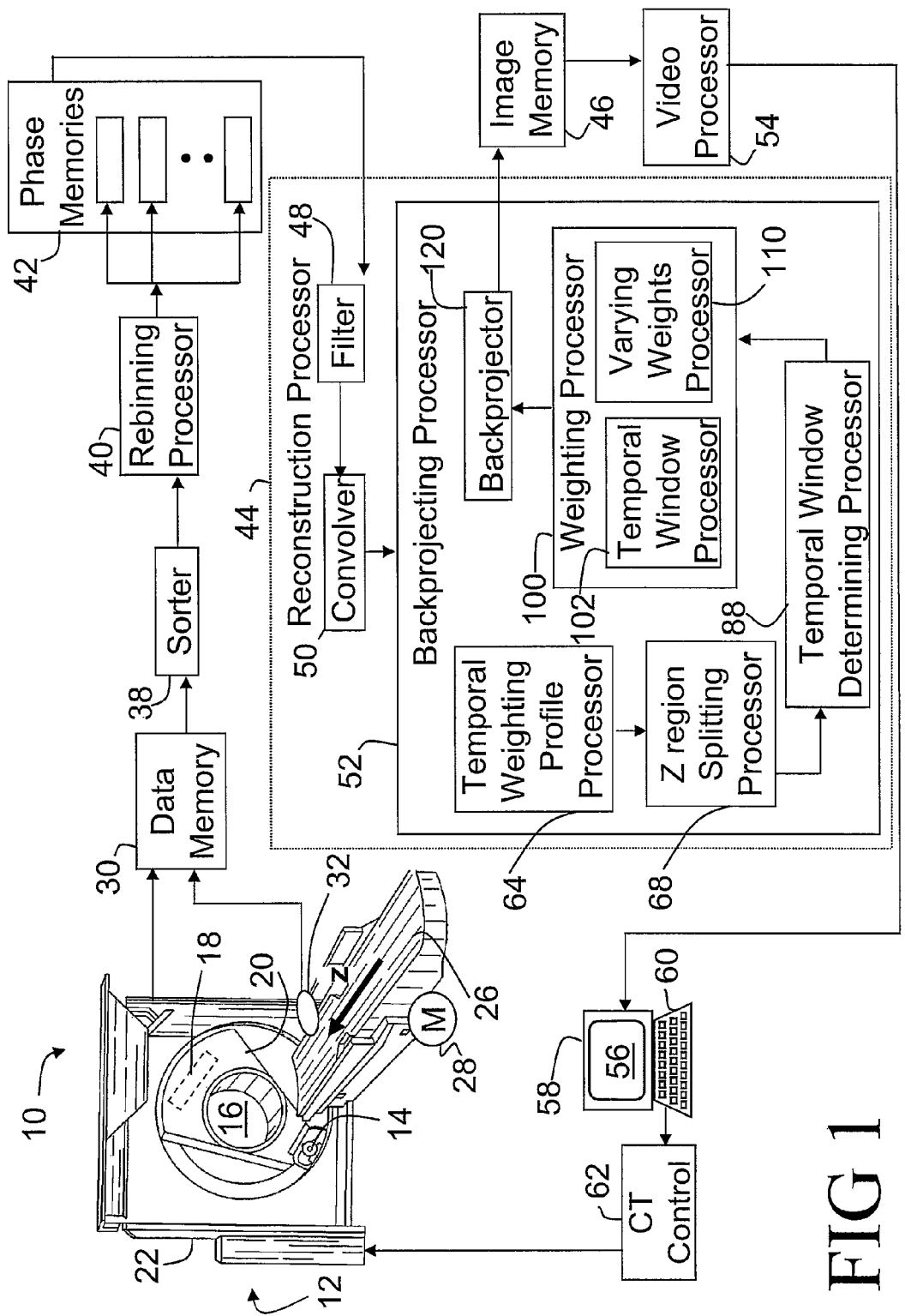

| | | | |
|---|---|---|---|
| 7,289,841 B2* | 10/2007 | Johnson et al. | 600/431 |
| 2004/0114708 A1 | 6/2004 | Bruder et al. | |
| 2004/0131140 A1 | 7/2004 | Bruder et al. | |
| 2004/0136490 A1 | 7/2004 | Edic et al. | |
| 2004/0175024 A1* | 9/2004 | Rasche et al. | 382/128 |
| 2005/0201598 A1* | 9/2005 | Harel et al. | 382/128 |

OTHER PUBLICATIONS

Hoffman, M.H.K. et al., "Noninvasive Coronary Angiography with 16-Detector REow CT: Effect of Heart Rate," Radiology Jan. 2005, 234(1), pp. 86-97.

Manzke, R., et al., "Artifact Analysis and Reconstruction Improvement in Helical Cardiac Cone Beam CT," IEEE Trans. on Med. Imaging, IEEE Service Center, Piscataway, NJ, USA, Sep. 2004, 23(9), pp. 1150-1164.

Kachelriess et al: "Extended Parallel Backprojection (EPBP) for Arbitrary Cone Angle and Arbitrary Pitch 3D and Phase-Correlated 4D CT Reconstruction"; Fully 3D'03, TU AM2-3, Proceedings of the VIIth International Conference on Fully 3D Reconstruciton in Radiology and Nuclear Medicine, Saint Malo, France, Jun. 29-Jul. 4, 2003, pp. 1-5.

Schecter et al: "Cardiac Image Reconstruction on a 16-Slice CT Scanner Using a Retrospectively ECG-Gated, Multi-Cycle 3D Back-Projection Algorithm"; Medical Imaging 2003:Image Processing, Proceedings of SPIE, 2003, vol. 5032, pp. 1820-1828.

\* cited by examiner

BANDS ARTIFACT REDUCTION FOR CARDIAC CT IMAGING

CROSS REFERENCE TO RELATED APPLICATIONS

This application claims the benefit of U.S. provisional application Ser. No. 60/695,753 filed Jun. 22, 2005, which is incorporated herein by reference.

The present application relates to the diagnostic imaging arts. It finds particular application in cardiac computed tomography imaging of a subject, and will be described with particular reference thereto. However, it may also find application in other types of computed tomography imaging, single photon emission computed tomography (SPECT), positron emission tomography (PET), three-dimensional x-ray imaging, and the like.

In general, a computed-tomography system comprises an x-ray source and an x-ray detector which rotates around an object to be examined. From several orientations, the object is irradiated with an x-ray beam from the x-ray source. The x-ray detector receives x-radiation that has passed through the object at the respective orientations and forms an attenuation profile for the orientation at issue. The attenuation profiles represent the attenuation of incident x-rays in the object due to and absorption or scattering of x-rays along the path of the x-rays through the object at the orientation at issue.

Helical cardiac cone beam images are reconstructed using phase selective algorithms. Typically, particular phases of the heart are chosen for cardiac image generation. Only data acquired close in time to the selected phases, i.e., the points in time corresponding to the same cardiac phase, but in different heart cycles, are used simultaneously in a multi-slice reconstruction process. Depending on the scan parameters, the patient's heart rate and its variability, the cardiac gating window width and position, a variable number of cycles is used for reconstruction of each of the voxels. Typically, the voxels are reconstructed from all available rays over all cardiac cycles which pass through a given voxel, i.e. an illumination window.

The quality of the CT image is often degraded by band artifacts resulting from the fact that voxels close in space to one another but having different axial position or Z coordinates are reconstructed using projections from the vicinity of the phase points of different heart cycles. Voxels at different Z coordinates can be illuminated over different groups of cardiac cycles or illumination windows. A first voxel is reconstructed using data acquired over one illumination window, while a second voxel is reconstructed using data acquired in a different illumination window. The number of cardiac cycles varies in different illumination windows. This can lead to a discrepancy between CT numbers which are calculated for the two voxels.

The views which are elongated along the Z direction, such as saggital or coronal view, may have streaks and artifacts which may be attributable to several causes such as non-periodic heart motion, inconsistent determination of the phase point within each heart cycle, different numbers of cardiac cycles contributing to various voxels, and others.

There is a need for a technique that suppresses band artifacts in cardiac cone beam imaging that does not depend on the correcting the source of the band artifacts. The present invention contemplates a method and apparatus that overcomes the aforementioned limitations and others.

According to one aspect of the present application, a diagnostic imaging system for imaging at a preselected phase point which occurs in one or more successive cardiac cycles as a subject moves in an examination region is disclosed. An illumination window illuminates each reconstructed voxel of the subject in phase point windows adjacent surroundingly the preselected phase point. A temporal window determining processor or algorithm determines a temporal window, which includes an integer number of phase points in successive cardiac cycles, in which the phase point windows are entirely included in the illumination window and truncates the illumination window in accordance with the determined temporal weighting profile. A Z region splitting processor or algorithm determines first and second regions of the temporal weighting profile along an axial direction with respect to the voxel Z-coordinate, the first and second regions alternating with one another. A weighting processor applies normalized weights to readings for the reconstructed voxels lying in the first and second regions of the temporal window. A backprojection processor or algorithm three-dimensionally backprojects the weighted readings into a volumetric image representation.

According to another aspect of the present application, an imaging method is disclosed. Each reconstructed voxel of a subject is illuminated in phase point windows adjacent surroundingly a preselected phase point, each phase point occurring in one or more successive cardiac cycles as the subject moves in an examination region. A temporal window, which includes an integer number of successive cardiac cycles, in which the phase point windows are entirely included in an illumination window, is determined. The illumination window is truncated in accordance with the determined temporal window. First and second regions in the temporal window along an axial direction are determined, the first and second regions alternating with one another. Readings for the reconstructed voxels lying in the first and second regions of the temporal window are weighted. The weighted readings are three-dimensionally backprojected into a volumetric image representation.

One advantage of the present application resides in reducing band artifacts.

Another advantage resides in a technique which avoids determining the source of the band artifacts.

Another advantage resides in improved images from cardiac and other gated imaging techniques.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 2:
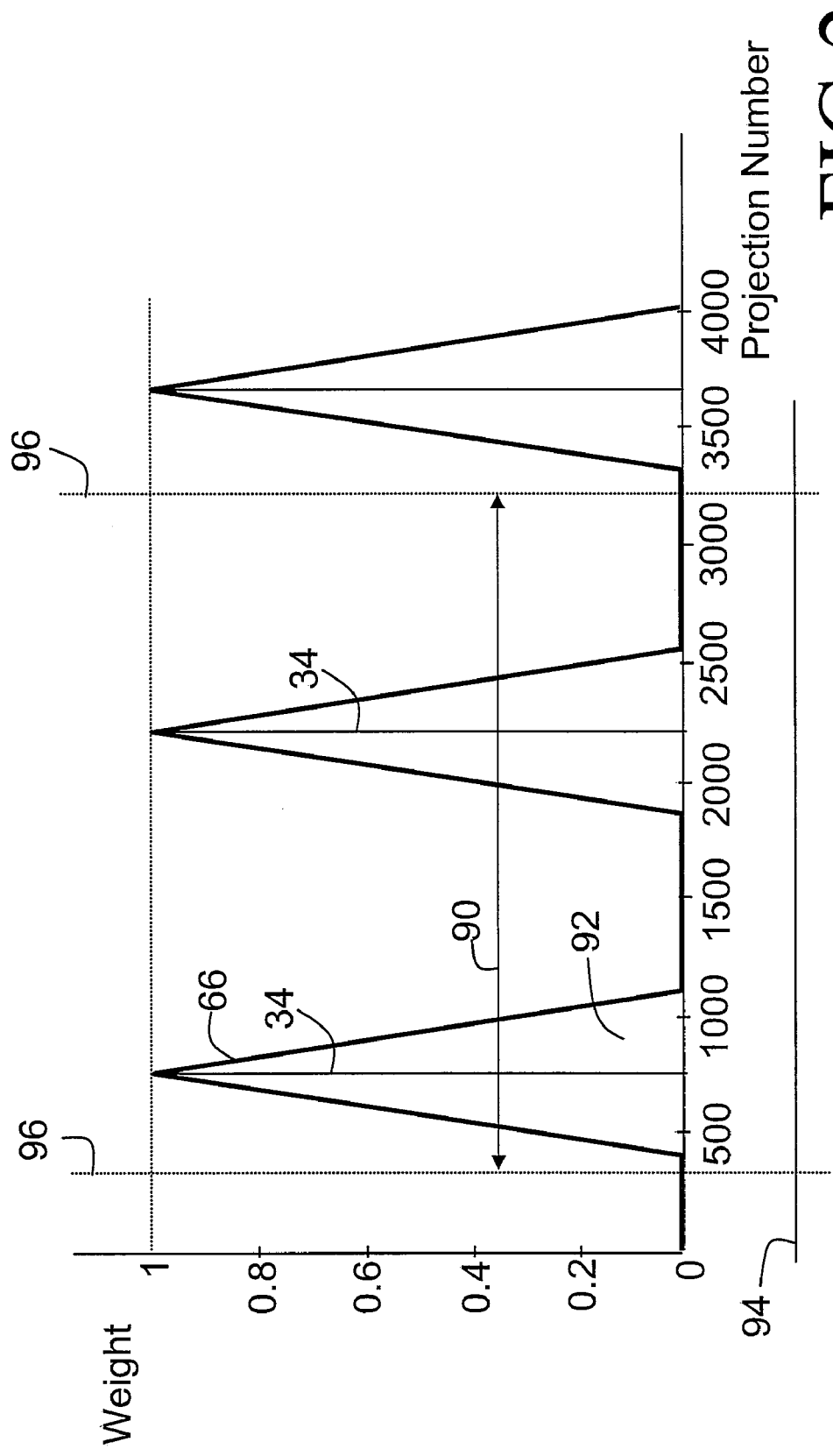

FIG. 1 diagrammatically shows a computed tomography imaging system;

FIG. 2 diagrammatically shows voxel-independent weighting profile; and

Figure 3:
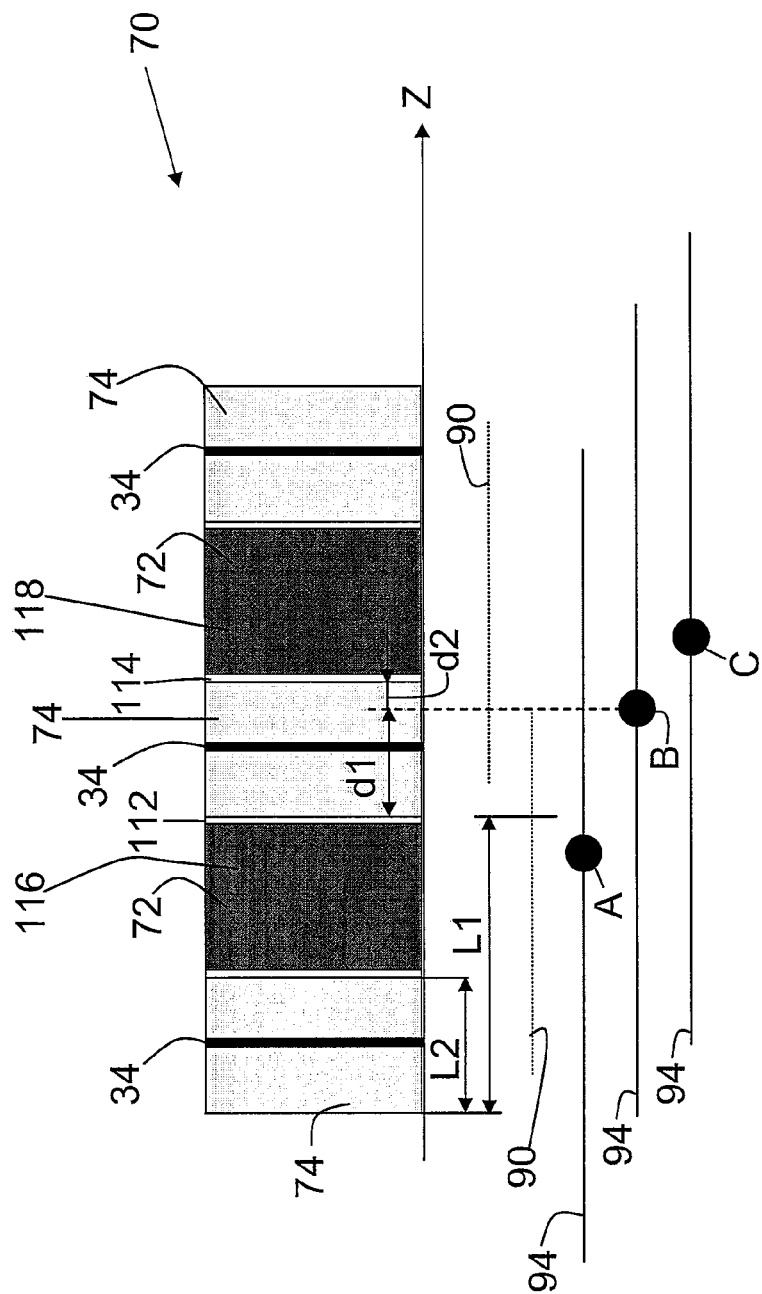

FIG. 3 diagrammatically shows a portion of a Z interval which is divided into alternate weighting profile regions.

With reference to FIG. 1, an imaging system 10 includes a computed tomography scanner 12 having a radiation source 14 that produces a radiation beam, preferably a cone or wedge beam, directed into an examination region 16. The radiation beam interacts with and is partially absorbed as it traverses a region of interest of an imaging subject disposed in the examination region 16, producing spatially varying absorption of the radiation as it passes through the examination region. A radiation detector 18, preferably a two-dimensional detector, detects the absorption-attenuated radiation after it passes through the examination region 16. The path between the source 14 and each of radiation detection elements of the detector 18 is denoted as a ray.

Preferably, the radiation source 14 produces a cone-beam of x-rays. The radiation source 14 and the detector 18 are preferably mounted in oppositely facing fashion on a rotating gantry 20 so that the detector 18 continuously receives x-rays from the radiation source 14. As the source 14 and the detector 18 rotate continuously about the examination region 16 on the rotating gantry 20, views are acquired over a plurality of rotations. Each view or two-dimensional array of data represents a cone of rays having a vertex at the source 14 collected by a concurrent sampling of the detection elements of the detector 18. In a helical cone beam computed tomography, a subject support or bed 26 is linearly moved in an axial or Z direction by a motor drive 28.

Optionally, cone beam computed tomography projection data are acquired over several rotations either (i) with the subject support 26 being stationary during each axial scan and stepped linearly between axial scans or (ii) with the subject support moving continuously to define a helical trajectory. The outputs of the detection elements of the radiation detector 18 are converted to electric acquired integrated attenuation projection values $\mu d_0$ that are stored in a data memory 30. Each projection datum $\mu d_0$ corresponds to a line integral of attenuation along a line from the radiation source 14 to a corresponding one of the detection elements of the detector 18.

For typical cone-beam geometries, the line integral index typically corresponds to a detector element used to measure the reading. It is contemplated, however, that the line integral index may lack a direct correspondence with detector element number. Such a lack of direct correspondence can result, for example, from interpolation between re-binned projections.

For a source-focused acquisition geometry in a multi-slice scanner, readings of the attenuation line integrals or projections of the projection data set stored in the data memory 30 can be parameterized as $P(\alpha,\beta,n)$, where $\alpha$ is the source angle of the radiation source 14 determined by the position of the rotating gantry 20, $\beta$ is the angle within the fan ($\beta \in [-\Phi/2, \Phi/2]$ where $\Phi$ is the fan angle), and n is the detector row number.

A cardiac monitor 32 monitors the patient's cardiac cycle and detects phase points 34 typically relative to the R-wave of each cycle, i.e. in each R-R interval. The position of the phase point 34 is selected by the clinician according to the motion characteristic of the heart and the required diagnostic information. A sorting means 38 sorts the attenuation data into data sets collected during each of the selected cardiac phases, i.e. cardiac phase specific data sets. A re-binning processor 40 re-bins the cardiac phase specific data from cone to parallel beam geometry into a set of parallel views. The parallel views are projected into the axial plane i.e., perpendicular to the rotation axis. Each view contains equidistant $\pi$-lines, where a $\pi$-line is defined as a line integral that is contained in the axial plane, intersecting the scan FOV and is characterized by the canonic coordinates $\theta_\pi, l$, where $\theta_\pi$ is an angle of propagation $\in [0, \pi)$, and l is a distance from an iso-center. Particularly for cardiac phases defined by a short temporal window, the data for one cardiac phase corresponds to data collected over short arc segments in each of a plurality of rotations and cardiac cycles. The arc segments of data individually are too small to be a full data set. To generate a full data set, data is collected over several cardiac cycles and, if necessary, interpolated. The cardiac phase specific data sets are stored in corresponding phase memories 42.

A reconstruction processor 44 processes the view data from the data for each selected cardiac phase into a corresponding three-dimensional image which is stored in an image memory 46. In one reconstruction technique, readings in each parallel projection are filtered with a filter 48. A convolver 50 performs a one-dimensional convolution with a ramp kernel such as 1D Jacobian kernel. The convolution is performed along a parallel set of readings. The data is convolved angle by angle to complete a 2D data set, covering the angular range of $\theta \in [0, \pi)$. Interpolation may be needed for a complete data set. A backprojecting processor 52 performs a normalized weighted backprojection of the convolved data into a 3D image representation as discussed in detail below. A video processor 54 processes some or all of the contents of the image memory 46 to create a human-viewable image representation such as a three-dimensional rendering, a selected image slice, a maximum intensity projection, a CINE animation, or the like. The human-viewable image representation is displayed on a display 56 of a user interface 58, which is preferably a personal computer, a workstation, a laptop computer, or the like. Optionally, selected contents of the image memory 46 are printed on paper, stored in a non-volatile electronic or magnetic storage medium, transmitted over a local area network or the Internet, or otherwise processed. Preferably, a radiologist or other operator controls the computed tomography imaging scanner 12 via an input means 60 to program a scan controller 62 to set up an imaging session, modify an imaging session, execute an imaging session, monitor an imaging session, or otherwise operate the scanner 12.

With continuing reference to FIG. 1 and further reference to FIG. 2, a temporal weighting profile processor or algorithm 64 calculates a voxel independent and projection-dependent temporal weighting profile 66 that is composed of a duplication of phase point windows, i.e., of the function $w'(c)$ that is centered in each heart cycle at the prespecified phase point 34:

$$w'(c) = \Lambda(c/\bar{c}), \text{ where}$$

$\Lambda$ is a triangle function with a peak equal to 1;
c is a shift in time between the reading and the phase point closest to the reading; and $\bar{c}$ is a half width of the phase point window contributing to the reconstruction.

The best resolution is obtained by seeking the minimal width for $\bar{c}$ that allows for a complete data set. The phase point window is calculated with a width that provides sufficient data for reconstruction of all the voxels.

With continuing reference to FIG. 1 and further reference to FIG. 3, a Z region splitting or weighting function determining means or processor or algorithm 68 splits a Z profile 70 into alternating first and second regions or fixed weight and changing weight regions 72, 74 in the axial direction Z. An axial length $L_1$ of each two adjacent first and second regions 72, 74 is defined as:

$$L_1 = v*RR, \text{ where}$$

v is a velocity of the bed;
RR is a heart period extracted from the patient's ECG.

The second regions 74 each is defined as surrounding the corresponding phase point 34. In one embodiment, each phase point 34, represented by a vertical line, lies substantially central in the associated second region 74. An axial length $L_2$ of the second region 74 is defined as:

$$L_2 = \gamma*v*RR, \text{ where}$$

$L_2$ is a length of the second region;
v is a velocity of the bed;
RR is a heart period extracted from the patient's ECG; and
$\gamma$ is a parameter which defines the length of the second regions within the heart period time.

The parameter α, which is selected as discussed above, sets the minimal value of the parameter γ:

$$\gamma = \alpha + \mathrm{mod}((WW_{min} - RT/2)/RR_{max} - \alpha, 1), \text{ where}$$

$WW_{min}$ is the minimal illumination window width from the set of windows that illuminate all the reconstructed voxels;
RT is the gantry rotation time; and
$RR_{max}$ is the maximal heart period during the scan.

With continuing reference to FIGS. 1 and 3 and reference again to FIG. 2, a temporal window determining algorithm or processor 88 determines a temporal window 90 for each corresponding reconstructed voxel A, B, C, . . . , . More specifically, the temporal window 90 is selected to include in the reconstruction only projections acquired from phase point windows 92 of an integer number N of successive phase points 34 which are entirely included in the illumination window 94 of the given voxel. The phase point windows, which are not entirely included in the illumination window 94 of the given voxel, are truncated as shown by lines 96. The narrow phase point window around each phase point 34 affords better resolution, but a low number of data points compromises image quality reconstruction.

The number N of successive phase points 34 is determined as follows:

$$N = \mathrm{floor}((WW_{min} - RT/2)/RR_{max} - \alpha), \text{ where}$$

$WW_{min}$ is the minimal illumination window width from the windows that illuminate all the reconstructed voxels;
RT is the gantry rotation time;
$RR_{max}$ is the maximal heart period during the scan; and
α is a parameter that is selected in advance and assumes typical values of 0.3-0.5.

In the example of FIG. 3, the number N of successive phase points 34 is equal to 2, e.g. the illumination window 94 is truncated to two phase point windows. In this manner, each of the illumination windows 94, which represent a range of motion over which each associated voxel in the first region 72 receives radiation, is replaced with the fixed temporal window 90 which corresponds to a precise number of cardiac cycles. Temporal weighting profile to either side of the temporal illumination window 90 is truncated.

A weighting processor 100 applies smoothly changing weights to all voxels with respect to the Z coordinate. More specifically, a fixed weighting or temporal window processor or algorithm 102 calculates normalized backprojection weights for the voxels which lie in the first regions 72, such as the voxels A, C. The fixed weighting processor 102 selects a segment of the temporal weighting profile 66 that falls under the voxel-dependent temporal window 90. The selected segment is normalized such that the sum of the weights given for all the projections that are folded into the same $\theta \in [0, \pi)$ is equal to 1. The total normalized weight given to each reading is:

$$W = W'(c)$$

A varying weight processor 110 applies a smoothly changing weighting to all voxels which lie in each second region 74, such as the voxel B. The normalized backprojection weighting applied for the voxel B in the second region 74 is calculated by linear interpolation between the normalized weighting profiles of the neighboring first regions 72. The weights of the interpolation are calculated according to distances d1, d2 between the Z coordinate of the voxel B and first and second borders 112, 114 of the second region 74 and adjacent corresponding leading and trailing first regions 116, 118.

A backprojector 120 or backprojection processor or algorithm back-projects the normalized projections into the image memory 46.

In this manner, by rounding the number of the phase points that contribute to the voxel to a precise fixed number of phase points for voxels in the first region and providing a continuous, smoothly changing normalized backprojection weighting with respect to the position of the voxels in the second region, the phenomenon of abrupt CT number change from one voxel to another in the Z direction is smoothed or substantially eliminated which results in suppressed artifacts.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A diagnostic imaging system for imaging at a preselected phase point which occurs in one or more successive cardiac cycles as a subject moves in an examination region, the imaging system comprising:
    an illumination window, which illuminates each reconstructed voxel of the subject in phase point windows adjacent surroundingly the preselected phase point;
    a temporal window determining processor or algorithm which determines a temporal window, which includes an integer number N of successive cardiac cycles, in which the phase point windows are entirely included in the illumination window, and truncating the illumination window in accordance with the determined temporal window;
    a Z-region splitting processor or algorithm which determines first and second regions along an axial direction, the first and second regions alternating with one another;
    a weighting processor which applies normalized weights to readings for the reconstructed voxels lying in the first and second regions of the temporal window; and
    a backprojection processor or algorithm for three-dimensionally backprojecting the normalized weighted readings into a volumetric image representation.

2. The system as set forth in claim 1, further including: a temporal weighting profile processor which determines a projection dependent temporal weighting profile and wherein the weighting processor includes: a temporal window processor which selects a segment of the temporal weighting profile which corresponds to the temporal window, and applies a fixed normalized weight of the selected segment to each voxel which lies in an associated first region.

3. The system as set forth in claim 2, wherein the weighting processor further includes: a varying weight processor for continuously and smoothly weighting the readings of each voxel which lies in an associated second region.

4. The system as set forth in claim 3, wherein the weight given to the voxel which lies in the associated second region is interpolated between the fixed weights which are given to the voxels which lie in associated leading and trailing first regions adjacent the corresponding second region.

5. The system as set forth in claim 1, further including:
    a rotating gantry;
    a source of a cone beam radiation which traverses the examination region and is disposed on the rotating gantry; and
    a radiation detector which is disposed on the rotating gantry oppositely the radiation source to detect the radiation after the radiation passes through the examination region and convert the detected radiation into an electronic projection data format.

6. The system as set forth in claim 5, wherein the number of successive cardiac cycles, which determines a size of the temporal window, is:

$$N=\text{floor}((WW_{min}-RT/2)/RR_{max}-\alpha), \text{ where:}$$

$WW_{min}$ is a minimal illumination window width from a set of illumination windows that illuminate the reconstructed voxels; RT is a gantry rotation time; $RR_{max}$ is a maximal heart period during the scan; and a is a parameter that is selected in advance.

7. The system as set forth in claim 1, wherein a length of each adjacent first and second regions is: $L_1=v*RR$, where
v is a velocity of the subject in the axial direction; and RR is a time period of the cardiac cycle.

8. The system as set forth in claim 1, wherein a length of the second region is equal to: $L_2=\gamma*v*RR$, where v is a velocity of the subject in the axial direction; RR is a time period of the cardiac cycle; and γ is a parameter which defines the length $L_2$ of the second region within the cardiac cycle.

9. The system as set forth in claim 1, further including:
a CT scanner, which acquires projection data within at least a plurality of illumination windows, the scanner including: a rotating gantry;
a source of a cone beam radiation which traverses an examination region;
a radiation detector which detects the radiation after the radiation passes through the examination region and converts the detected radiation into the projection data format, which radiation source and radiation detector are oppositely positioned at the rotating gantry for continuous rotation about the examination region; and
a display for displaying the volumetric image representation.

10. An imaging method, comprising:
illuminating each reconstructed voxel of a subject in phase point windows adjacent surroundingly a preselected phase point, each phase point occurring in one or more successive cardiac cycles as the subject moves in an examination region;
determining a temporal window, which includes an integer number of successive cardiac cycles, in which the phase point windows are entirely included in an illumination window, and truncating the illumination window in accordance with the determined temporal window;
determining first and second regions in the temporal window along an axial direction, the first and second regions alternating with one another;
applying normalized weights to readings for the reconstructed voxels lying in the first and second regions of the temporal window; and
three-dimensionally backprojecting the normalized weighted readings into a volumetric image representation.

11. The method as set forth in claim 10, further including:
determining a projection dependent temporal weighting profile; selecting a segment of the temporal weighting profile which corresponds to the temporal window; and
applying a common normalized weight of the selected segment to each voxel which lies in an associated first region.

12. The method as set forth in claim 11, wherein the step of weighting further includes:
applying a continuously and smoothly varying weight to each voxel which lies in an associated second region.

13. The method as set forth in claim 12, wherein the weight given to a voxel which lies in the associated second region is interpolated between the weights which are given to voxels which lie in associated first regions adjacent the corresponding second region.

14. The method as set forth in claim 10, further including:
rotating a cone beam radiation around the examination region; and
detecting the radiation which has traversed the subject.

15. The method as set forth in claim 14, wherein the number of successive cardiac cycles corresponding to the temporal window is:

$$N=\text{floor}((WW_{min}-RT/2)/RR_{max}-\alpha), \text{ where:}$$

$WW_{min}$ is a minimal illumination window width from a set of illumination windows that illuminate the reconstructed voxels; RT is a gantry rotation time; $RR_{max}$ is a maximal heart period during the scan; and α is a parameter that is selected in advance.

16. The method as set forth in claim 10, wherein a length of the adjacent first and second regions is equal to:

$$L_1=v*RR, \text{ where}$$

v is a velocity of the subject;
RR is a time period of the cardiac cycle.

17. The method as set forth in claim 10, wherein a length of the second region is:

$$L_2=\gamma*v*RR, \text{ where}$$

v is a velocity of the subject; RR is a time period of the cardiac cycle; and .gamma, is a parameter which defines the length $L_2$ of the second region within the cardiac cycle.

18. A CT scanner for performing the steps of claim 10.

19. A diagnostic imaging system including:
a source of a cone beam radiation which traverses an examination region;
a radiation detector which detects the radiation after the radiation passes through the examination region and converts the detected radiation into an electronic projection data format;
an image processor which reconstructs the cone beam projection data into a three-dimensional reconstructed image which image processor is programmed to perform steps of:
sorting the projection data into data sets collected during each of selected cardiac cycles,
re-binning the collected data into a parallel ray format,
filtering the parallel ray format data,
convolving the filtered data,
determining a temporal window, which includes an integer number of successive cardiac cycles, and
determining a projection dependent temporal weighting profile;
determining first and second regions in the temporal window along an axial direction, the first and second regions alternate with one, another:
selecting a segment of the temporal weighing profile which corresponds to the temporal window;
applying a normalized common weight of the selected segment of the temporal weighting profile to readings of each voxel which lies in an associated first region, and continuously weighting the readings of each voxel which lies in an associated second region; and
a display which displays the convolved normalized weighted backprojected data in a human-viewable image format.

20. A method of cardiac imaging comprising:
- traversing an examination region with a source of a cone beam radiation;
- detecting the radiation after the radiation passes through the examination region and converts the radiation into an electronic projection data format;
- reconstructing the cone beam projection data into a three-dimensional reconstructed image, wherein the reconstructing includes:
  - sorting the projection data into data sets collected during each of selected cardiac cycles;
  - re-binning the collected data into a parallel ray format, filtering the parallel ray format data;
  - convolving the filtered data;
  - determining a temporal window, which includes an integer number of successive cardiac cycles; and
  - determining a projection dependent temporal weighting profile;
  - determining first and second regions in the temporal window along an axial direction, wherein the first and second regions alternate with one another;
  - selecting a segment of the temporal weighing profile which corresponds to the temporal window,
  - applying a normalized common weight of the selected segment of the temporal weighting profile to readings of each voxel which lies in an associated first region,
  - continuously weighting the readings of each voxel which lies in an associated second region; and
  - displaying the convolved normalized weighted back-projected data in a human-viewable image format.

* * * * *